(12) United States Patent
Wiktor et al.

(10) Patent No.: US 11,246,969 B2
(45) Date of Patent: Feb. 15, 2022

(54) APPARATUS FOR EXTRACORPOREAL BLOOD TREATMENT AND METHOD FOR OPERATING AN EXTRACORPOREAL BLOOD TREATMENT APPARATUS

(71) Applicant: FRESENIUS MEDICAL CARE DEUTSCHLAND GMBH, Bad Homburg (DE)

(72) Inventors: Christoph Wiktor, Gelnhausen (DE); Arne Peters, Bad Homburg (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 1113 days.

(21) Appl. No.: 15/104,140

(22) PCT Filed: Dec. 2, 2014

(86) PCT No.: PCT/EP2014/076300
§ 371 (c)(1),
(2) Date: Jun. 13, 2016

(87) PCT Pub. No.: WO2015/086382
PCT Pub. Date: Jun. 18, 2015

(65) Prior Publication Data
US 2016/0310655 A1    Oct. 27, 2016

(30) Foreign Application Priority Data

Dec. 13, 2013 (DE) ............... 10 2013 021 012.7

(51) Int. Cl.
*A61M 1/34* (2006.01)
*A61M 1/16* (2006.01)

(52) U.S. Cl.
CPC ............ *A61M 1/3427* (2014.02); *A61M 1/16* (2013.01); *A61M 1/1601* (2014.02);
(Continued)

(58) Field of Classification Search
None
See application file for complete search history.

(56) References Cited

U.S. PATENT DOCUMENTS 4,209,391 A * 6/1980 Lipps .................. A61M 1/16
210/647
4,676,905 A * 6/1987 Nagao .................. A61M 1/16
210/321.65
(Continued)

FOREIGN PATENT DOCUMENTS

DE 102010023635 A1 * 12/2011 .......... A61M 1/1635
EP 0226122 A2 * 6/1987 ............ F04B 43/067
(Continued)

OTHER PUBLICATIONS

International Preliminary Report on Patentability from International Search Report from PCT/EP2014/076300, dated Jun. 23, 2016.
(Continued)

*Primary Examiner* — Bobby Ramdhanie
*Assistant Examiner* — Denise R. Anderson
(74) *Attorney, Agent, or Firm* — Kilyk & Bowersox, P.L.L.C.

(57) ABSTRACT

A device for extracorporeal blood treatment and a method for operating an extracorporeal blood treatment device provide for an ultrafiltrate pump of an ultrafiltration apparatus to be operated in a first and second operating mode. The ultrafiltrate pump is operated in the first operating mode in such a way that the pressure on the blood-side of the semipermeable membrane is higher than the pressure on the dialysate-side of the semipermeable membrane of a dialyser, so that during the first operating mode a predetermined amount of fluid is removed from an extracorporeal blood circuit via the semipermeable membrane of the dialyser. In the second operating mode, the ultrafiltrate pump is operated
(Continued)

in such a way that the pressure on the blood-side of the semipermeable membrane is, at successive intervals, alternately higher and lower than the pressure on the dialysate-side of the semipermeable membrane of the dialyser, so that fluid is continuously removed from and supplied to the extracorporeal blood circuit via the semipermeable membrane (push/pull mode). Additional components, in particular a separate push/pull pump, are not required for operation of the blood treatment device in push/pull mode. This results in both lower dimensions and lower weight. Operation in push/pull mode can increase the service life of the dialyser and the clearance of the dialysis treatment can also be increased for certain substances.

9 Claims, 3 Drawing Sheets

(52) U.S. Cl.
CPC .......... *A61M 1/165* (2014.02); *A61M 1/1635* (2014.02); *A61M 1/1672* (2014.02); *A61M 1/342* (2013.01); *A61M 1/3465* (2014.02); *A61M 2205/50* (2013.01); *A61M 2205/7554* (2013.01)

(56) References Cited

U.S. PATENT DOCUMENTS

| | | | |
|---|---|---|---|
| 5,011,607 A * | 4/1991 | Shinzato | A61M 1/16 210/110 |
| 5,863,421 A | 1/1999 | Peter, Jr. et al. | |
| 7,871,390 B2 | 1/2011 | Rambod et al. | |
| 2011/0132838 A1 | 6/2011 | Curtis et al. | |
| 2013/0087210 A1 * | 4/2013 | Brandl | A61M 1/1694 137/2 |
| 2013/0213890 A1 * | 8/2013 | Kelly | A61M 1/3612 210/646 |
| 2015/0129498 A1 * | 5/2015 | Mishima | G01M 3/2846 210/646 |

FOREIGN PATENT DOCUMENTS

| | | | | |
|---|---|---|---|---|
| EP | 0 668 793 B1 | 8/1995 | | |
| EP | 1 867 353 A1 | 12/2007 | | |
| JP | WO-2013180154 A1 * | 12/2013 | ............. | A61M 1/14 |
| WO | 1994-11093 A1 | 11/1993 | | |
| WO | 2011-157396 A1 | 12/2011 | | |

OTHER PUBLICATIONS

International Search Report from PCT/EP2014/076300, dated Feb. 18, 2015.
Shinzato et al., "Alternate repetition of short-fore- and backfiltrations reduces convective albumin loss," Kidney International, vol. 50 (1996) pp. 432-435.

* cited by examiner

APPARATUS FOR EXTRACORPOREAL BLOOD TREATMENT AND METHOD FOR OPERATING AN EXTRACORPOREAL BLOOD TREATMENT APPARATUS

CROSS REFERENCE TO RELATED APPLICATIONS

The present application is the national stage entry of International Patent Application No. PCT/EP2014/076300, filed on Dec. 2, 2014, the disclosure of which is expressly incorporated herein by reference in its entirety, and which claims priority to German Application DE 10 2013 021 012.7, filed on Dec. 13, 2013.

FIELD OF INVENTION

The present invention relates to a device for extracorporeal blood treatment and to a method for operating a device for extracorporeal blood treatment.

BACKGROUND

Known blood treatment devices have a dialyser or filter which is divided by a semipermeable membrane into a blood chamber and a dialysate chamber. The patient's blood flows through the blood chamber of the dialyser in an extracorporeal blood circuit, whereas the dialysate flows through the dialysate chamber of the dialyser in a dialysate circuit.

With known blood treatment devices, fluid can be removed from or supplied to the patient during extracorporeal blood treatment via the semipermeable membrane of the dialyser. Fluid is removed from the patient (ultrafiltration) if the pressure on the blood-side of the semipermeable membrane is higher than the pressure on the dialysate-side of the membrane. If, by contrast, the pressure is lower on the blood-side than on the dialysate-side, fluid is supplied to the patient.

U.S. Pat. No. 5,011,607 A1 describes a particular variant of extracorporeal blood treatment, in which the blood treatment device is operated using an oscillating transmembrane pressure, so that fluid is alternately removed from the extracorporeal blood circuit and supplied to the extracorporeal blood circuit via the semipermeable membrane of the dialyser. This means that deposits can detach themselves from the membrane.

The dialysis device described in U.S. Pat. No. 5,011,607 A1 has a feed line leading to the dialysate chamber of the dialyser and a discharge line leaving the dialysate chamber, a first dialysate pump for conveying dialysate into the dialysate chamber arranged in the feed line and a second dialysate pump for conveying dialysate fluid from the dialysate chamber arranged in the discharge line. If the conveyance rates of the two dialysate pumps are equal, fluid is neither removed from nor supplied to the patient. The dialysis device has a positive displacement pump having a pumping chamber in which a positive displacement element is arranged. The pumping chamber of the reciprocating pump is in fluid communication with the feed line. When the reciprocating pump is running, an oscillating transmembrane pressure is generated, so that at short time-intervals, i.e. in the suction phase and pressure phase of the pump, a certain amount of fluid is removed from and supplied to the extracorporeal blood circuit respectively. This dialysis variant is also known as push/pull dialysis.

U.S. Pat. No. 5,011,607 A1 also describes an alternative configuration in which an oscillating transmembrane pressure is generated without an additional push/pull pump. In the alternative configuration, the two dialysate pumps are operated alternately at different conveyance rates to generate the oscillating transmembrane pressure.

In order to be able to remove fluid from the patient over the entire duration of the extracorporeal blood treatment, known blood treatment devices have an ultrafiltration apparatus, which has an ultrafiltration pump used to take fluid (ultrafiltrate) away from the dialysate system.

A blood treatment device comprising an ultrafiltration apparatus providing for operation in push/pull mode is disclosed in Replacement of renal function by dialysis, 5th ed./edited by Walter H. Hörl et al., ISBN 1-4020-0083-9, pages 388 and 389 (FIG. 42). The disclosed dialysis device also has both an ultrafiltrate pump and a push/pull pump, there being fluid communication between the ultrafiltrate pump and the dialysate discharge line, and the push/pull pump and the dialysate feed line.

SUMMARY

The object of the present invention is to simplify operation of a blood treatment device in push/pull mode.

This object is achieved according to the device for extracorporeal blood treatment and method of operating a device for extracorporeal blood treatment of the present invention.

The simplification of the design of the device, according to the present invention, for extracorporeal blood treatment is based on the ultrafiltrate pump of the ultrafiltration apparatus being operated in a first and second operating mode.

In the first operating mode, the ultrafiltrate pump is operated in such a way that the pressure on the blood-side of the semipermeable membrane is higher than the pressure on the dialysate-side of the semipermeable membrane of the dialyser, so that during the first operating mode a predetermined amount of fluid is removed from the extracorporeal blood circuit via the semipermeable membrane of the dialyser.

In the second operating mode, the ultrafiltrate pump is operated in such a way that the pressure on the blood-side of the semipermeable membrane is, at successive intervals, alternately higher and lower than the pressure on the dialysate-side of the semipermeable membrane of the dialyser, so that fluid is continuously removed from and supplied to the extracorporeal blood circuit via the semipermeable membrane (push/pull mode).

Therefore, the device according to the present invention and the method according to the present invention do not require additional components, in particular a separate push/pull pump, for operation in push/pull mode. This results in both smaller dimensions for the dialysis machine and a lower weight. Operation in push/pull mode can increase the service life of the dialyser since deposits detach themselves from the semipermeable membrane of the dialyser. In addition, clearance of the dialysis treatment can also be increased for certain substances.

Another advantage is that the change in the volume (push/pull volume) is linked not to the conveyance rate of a separate push/pull pump but to the conveyance rate of the ultrafiltrate pump, which is involved in balancing fresh and used dialysate.

The relevant operating mode can be selected with the device according to the invention using an input unit, which may also be part of a menu navigation.

The ultrafiltrate pump is preferably a positive displacement pump having a pumping chamber in which a movable positive displacement element is arranged. The positive displacement pump is preferably a reciprocating pump or a membrane pump, which can be used to convey a precisely determined volume.

In the first operating mode, the pumping chamber of the positive displacement pump is in fluid communication with the dialysate system in a suction phase and with a drain in a subsequent pressure phase. In the second operating mode, the pumping chamber of the positive displacement pump is in fluid communication with the dialysate system in both the suction phase and the pressure phase, whereas the fluid communication from the pumping chamber to the drain is shut.

Another preferred embodiment provides that the dialysate system comprises a balancing apparatus which may have one or more balancing chambers. Fresh dialysate is supplied to the balancing apparatus via a first feed line from a dialysate source. Used dialysate is carried away from the balancing apparatus via a discharge line into a drain. A second discharge line leads away from the balancing apparatus and to the dialysate chamber of the dialyser, and a second feed line leads from the dialysate chamber to the balancing apparatus. In this embodiment the positive displacement pump is joined to an ultrafiltrate line which branches off from the second feed line and leads to the drain.

Switching between the first and second operating mode preferably takes place by means of obturating members, which are arranged in the ultrafiltrate line respectively upstream of and downstream from the positive displacement pump. The control unit for controlling the positive displacement pump and the obturating members may be components of the central control unit of the blood treatment device.

A particularly preferred embodiment provides a dialysate system having a dialysate circuit which includes the dialysate chamber of the dialyser and in which the dialysate is conveyed repeatedly through the dialysate chamber while fresh and used dialysate is supplied to the dialysate system in a balanced manner. In this embodiment the blood treatment device is advantageously operated in the second operating mode when the dialysate is recirculating in the dialysate circuit.

In the following description, embodiments of the invention are explained in more detail with reference to the drawings.

DETAILED DESCRIPTION

Figure 1:
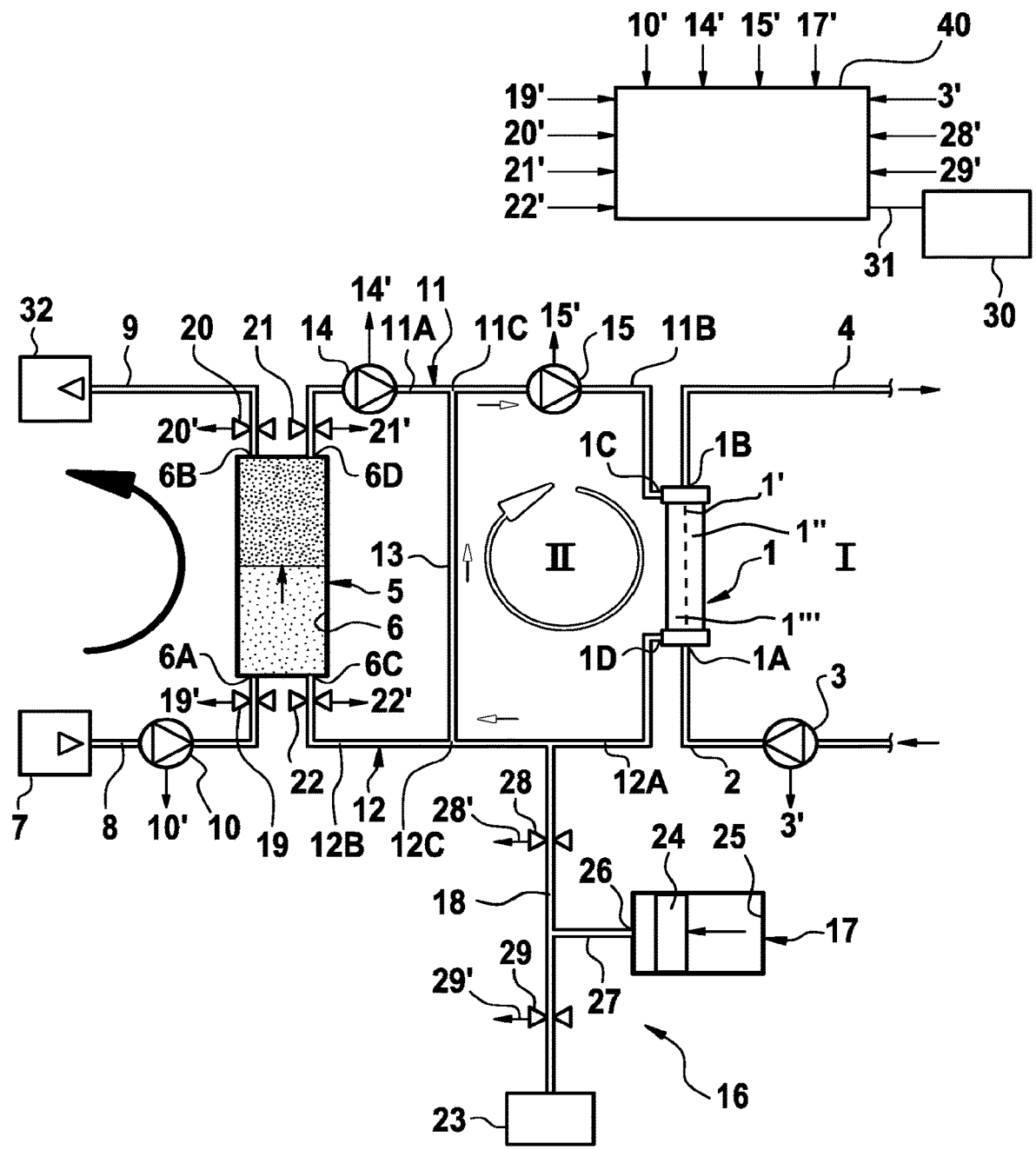
FIG. 1 is a highly simplified schematic view of an embodiment of the blood treatment device according to the invention, showing the first operating phase of an operating cycle.

The blood treatment device has a dialyser 1 which is divided by a semipermeable membrane 1' into a blood chamber 1" and a dialysate chamber 1'''. A blood supply line 2, into which a blood pump 3 is connected, leads from the patient to an inlet 1A to the blood chamber 1" of the dialyser 1, whereas a blood removal line 4, which leads to the patient, leads away from an outlet 1B of the blood chamber 1" of the dialyser 1. During blood treatment, the patient's blood flows, in the extracorporeal blood circuit I, through the blood chamber 1" of the dialyser 1.

To balance fresh dialysate out against used dialysate, a balancing apparatus 5 is provided which has just one balancing chamber 6 in the present embodiment. The balancing chamber 6 has a first inlet 6A at the bottom and a first outlet 6B at the top, and a second inlet 6C at the bottom and a second outlet 6D at the top.

The fresh dialysate is provided in a dialysate source 7. A first feed line 8 leads away from the dialysate source 7 and leads to the first inlet 6A to the balancing chamber 6. A first discharge line 9 leads away from the first outlet 6B of the balancing chamber 6 and leads to a drain 32. A dialysate pump 10, in particular an occluding pump, is connected into a first feed line 8 and conveys fresh dialysate from the dialysate source 7 into the blood chamber 6.

A second discharge line 11 leads away from the second outlet 6D of the balancing chamber 6 and leads to the inlet 1C of the dialysate chamber of the dialyser 1. A second feed line 12 leads away from the outlet 1D of the dialysate chamber and leads to the second inlet 6C of the balancing chamber 6.

The feed and discharge lines 8, 9, 11 and 12 are tubular lines, which may also be formed as channels in a replaceable unit. The second discharge line 11 has a first portion 11A and a second portion 11B in the direction of flow, whereas the second feed line 12 has a first portion 12A and a second portion 12B in the direction of flow.

The second discharge line 11 and the second feed line 12 are connected by means of a bypass line 13 which is joined via one end to the connection point 11C between the first portion 11A and the second portion 11B of the second discharge line 11 and via the other end to the connection point 12C between the first portion 12A and the second portion 12B of the second feed line 12.

The bypass line 13 creates a fluid circuit II which includes the dialysate chamber of the dialyser 1. The fluid circuit II comprises the bypass line 13, the second portion 11B of the second discharge line 11, the dialysate chamber of the dialyser 1 and the first portion 12A of the second feed line 12.

A second pump 14 is connected into the first portion 11A of the second discharge line 11 and a third pump 15 is connected into the second portion 11B of the second discharge line 11.

The blood treatment device has an ultrafiltration apparatus 16 having an ultrafiltrate pump 17 which is used to remove fluid (ultrafiltrate) from the extracorporeal blood circuit I.

The ultrafiltrate pump 17 is joined to an ultrafiltrate line 18 which leads away from the first portion 12A of the second feed line 12. The ultrafiltrate line 18 leads to a drain 23, which might be a canister for example.

In the present embodiment the ultrafiltrate pump 17 is a reciprocating pump which has a pumping chamber in which a piston 24 is arranged so as to be longitudinally displaceable. The pumping chamber 25 has an inlet/outlet 26 which is joined by means of a joining line 27 to the ultrafiltrate line 18. The pumping chamber is therefore in fluid communication with the ultrafiltrate line.

The pumps 3, 10, 14, 15, 17 are connected by means of control lines 3', 10', 14', 15', 17' to a control unit 40. The control unit 40 is a component of the central control unit of the dialysis device in the present example.

A first obturating member 19 is connected into the first feed line 8 between the first pump 10 and the balancing chamber 6, whereas a second obturating member 20 is connected into the first discharge line 9. A third obturating member 21 is connected into the second discharge line 11 between the balancing chamber 6 and the second pump 14, whereas a fourth obturating member 22 is connected into the second feed line 12 between the connection point 12C and the balancing chamber 6.

A fifth obturating member 28 is connected into the portion of the ultrafiltrate line 18 upstream of the point at which the joining line 27 joins the ultrafiltrate line, and a sixth obturating member 29 is connected into the portion of the ultrafiltrate line downstream from the joining line.

In a first embodiment, the obturating members 19, 20, 21, 22, 28, 29 are electromagnetically actuatable tube clamps which are connected by means of control lines 19', 20', 21', 22', 28', 29' to the central control unit 40. In a second embodiment comprising a replaceable unit in which the feed and discharge lines are formed as channels, the obturating members may be valves.

To operate the blood treatment device, the control unit 40 controls the pumps 10, 14, 15 and the obturating members 19, 20, 21, 22 as follows. The dialysis device is operated in successive cycles, each comprising two operating phases. FIG. 1 shows the first operating phase and FIG. 2 shows the second operating phase of an operating cycle.

The first operating phase involves filling the balancing chamber 6 while dialysate flows through the dialyser 1. The central control unit 40 opens the first and second obturating members 19, 20 and shuts the third and fourth obturating members 21, 22. As it does so, the control unit 40 sets the first pump 10 and the third pump 15 in operation. The second pump 14 is in the stop condition. Since the second pump 14 is an occluding pump, the third obturating member 21 can also be open.

The first pump 10 conveys fresh dialysate from the dialysate source 7 into the balancing chamber 6, which has been filled with used dialysate in the second operating phase of the preceding operating cycle. As the balancing chamber 6 is filling up with fresh dialysate, the used dialysate rejected via the first discharge line 9 into the drain 32. The first pump 10 keeps running until all the used dialysate in the balancing chamber 6 has been replaced with fresh dialysate. As the balancing chamber 6 is being filled with fresh dialysate, the fluid flows uninterruptedly through the dialyser 1. The third pump 15 conveys the dialysate in the fluid circuit II, which includes the second portion 11B of the second discharge line 11, the dialyser 1, the first portion 12A of the second feed line 12 and the bypass line 13 (FIG. 1).

Figure 2:
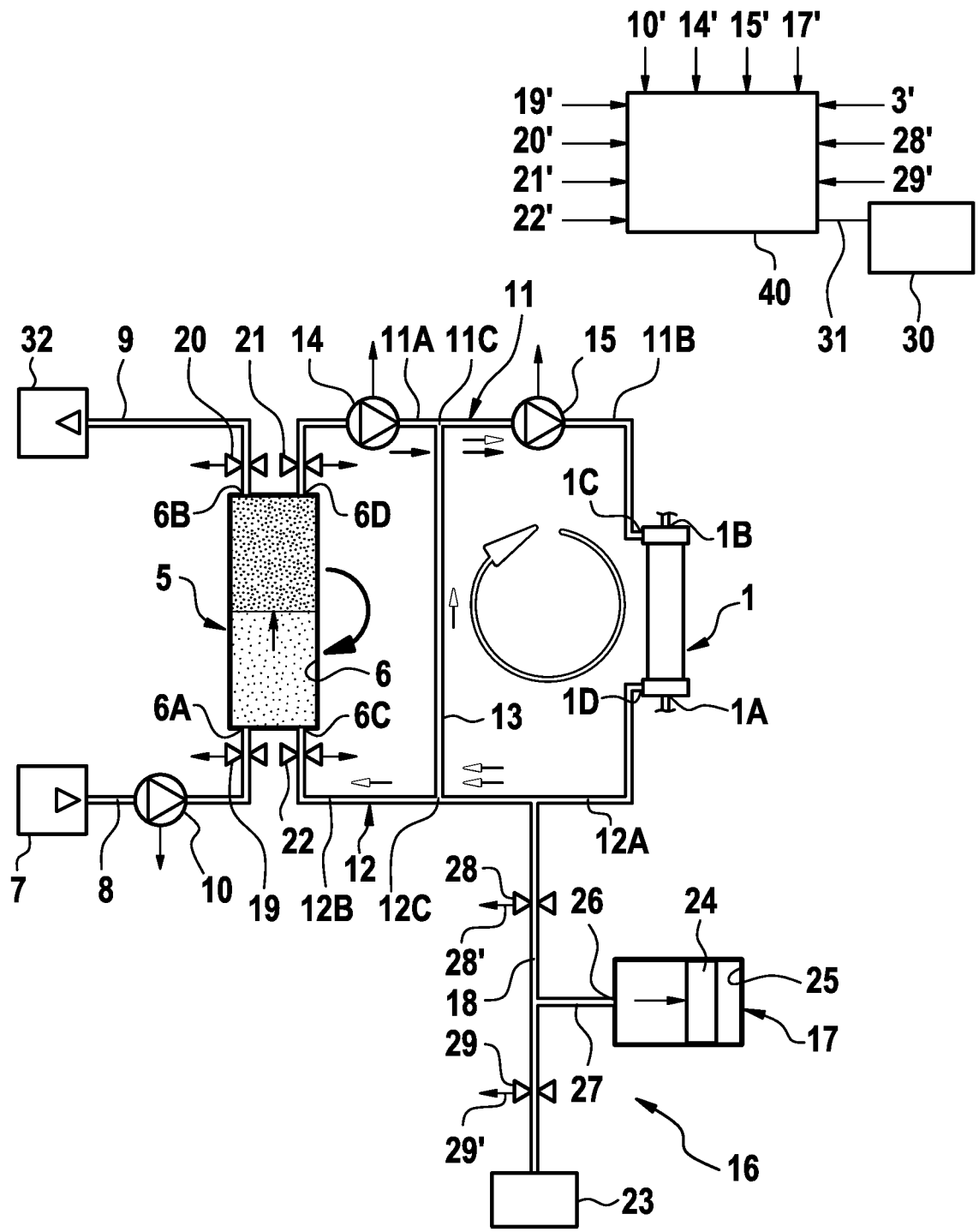
FIG. 2 shows the blood treatment device in FIG. 1, showing the second operating phase of the operating cycle.

The first operating phase (FIG. 1) is followed by the second operating phase (FIG. 2). In the second operating phase, the central control unit 40 shuts the first and second obturating members 19, 20 and opens the third and fourth obturating members 21, 22. Furthermore, the control unit 40 stops the first pump 10 and sets the second pump 14 in operation. As a result, the second and third pumps 14, 15 are running. The control unit 40 sets a lower conveyance rate for the second pump 14 than for the third pump 15. As a result, dialysate flows in the fluid circuit II at a flow rate corresponding to the difference between the conveyance rates of the third and second pumps 15, 14. These conveyance rates $QD_{fast}$ may be relatively high.

As the dialysate circulates through the dialyser 1 in the fluid circuit II, the fluid circuit II is supplied constantly with fresh dialysate and used dialysate is removed from said fluid circuit. The fresh dialysate is fed at the conveyance rate preset by the second pump 14 via the first portion 11A of the second discharge line 11, which is joined to the second outlet 6D of the balancing chamber 6, to the fluid circuit II.

Depending on the conveyance rates of the second and third pumps 14, 15, fresh dialysate can be supplied continuously over a relatively short or a relatively long period, and the desired ratio of fresh to used dialysate can be adjusted in the fluid circuit II.

The second operating phase (FIG. 2) is then followed once again by the first operating phase (FIG. 1) of a subsequent cycle.

Other embodiments of the blood treatment device are described in WO 2011/157396.

The blood treatment device has an input unit 30 which is connected via a data line 31 to the control unit 40. The input unit 30 can be used to select a first or second operating mode while the blood treatment device is being operated as described above.

For the first operating mode, the control unit 40 starts the reciprocating pump 17. In the suction phase of the pump 17, the control unit 40 opens the fifth obturating member 28 and shuts the sixth obturating member 29, and in the pressure phase the control unit 40 shuts the fifth obturating member and opens the sixth obturating member, so that ultrafiltrate is removed from the extracorporeal blood circuit I during the suction phase and carried away into the drain during the pressure phase.

For the second operating mode, the control unit 40 starts the reciprocating pump 17, opens the fifth obturating member 28 and shuts the sixth obturating member 29. The movement of the piston 24 of the reciprocating pump 17 results in the generation of an oscillating transmembrane pressure. A volume of fluid corresponding to the volume of the pumping chamber 25 is alternately removed from and supplied to the extracorporeal blood circuit I via the semipermeable membrane of the dialyser 1, whereby deposits on the semipermeable membrane get detached. Moreover, the clearance of the dialysis treatment is increased for certain substances.

The blood treatment device is preferably operated in the second operating mode (push/pull mode) while the dialysate is circulating in the dialysate circuit II.

Figure 3:
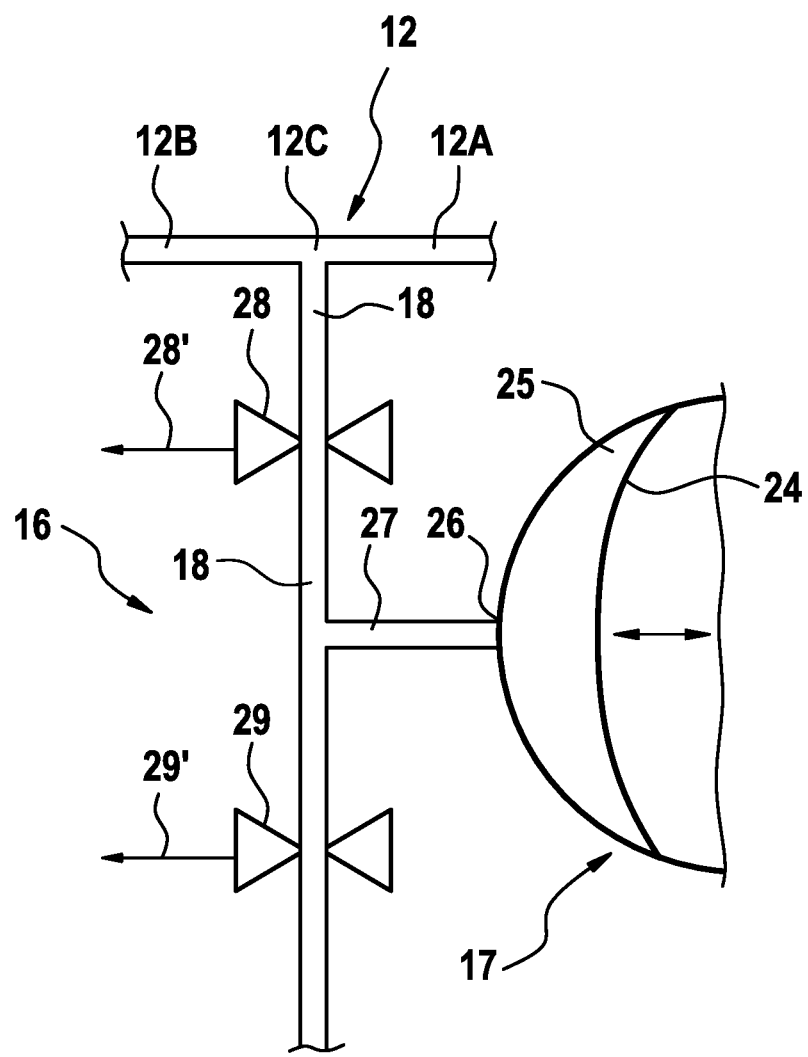
FIG. 3 shows an alternative embodiment of the positive displacement pump of the ultrafiltration apparatus.

FIG. 3 shows an alternative embodiment of the positive displacement pump 17, with corresponding parts having been assigned like reference numerals. The positive displacement pump 17 in FIG. 3 is a membrane pump having a pumping chamber 25 in which a flexible membrane 24 is arranged as the positive displacement element. The flexible membrane has a predetermined pressure applied to it by means of a pressure source (not shown), so that fluid in the pumping chamber 25 is either sucked up or displaced. This makes it possible to generate pressure pulses in the dialysate system in a controlled manner, so that fluid is alternately removed from or supplied to the extracorporeal blood circuit I via the membrane of the dialyser. In other respects the membrane pump corresponds to the reciprocating pump in terms of function.

The invention claimed is:

1. An extracorporeal blood treatment device comprising:
    a dialyser comprising a blood chamber, a dialysate chamber, a blood chamber inlet, a blood chamber outlet, a dialysate chamber inlet, a dialysate chamber outlet, and a semipermeable membrane, the blood chamber and the dialysate chamber being divided from one another by the semipermeable membrane, the dialyser being configured to enable blood to flow through the blood chamber and dialysate to flow through the dialysate chamber, to treat the blood,
    an extracorporeal blood circuit comprising a blood pump and the blood chamber of the dialyser, and a dialysate circuit comprising a dialysate pump, the dialysate chamber of the dialyser, an ultrafiltration apparatus, a first drain, a second drain, a first obturating member, a second obturating member, a balancing apparatus, a first feed line that leads to the balancing apparatus and is configured to supply dialysate from a dialysate source into the balancing apparatus, a first discharge line that leads away from the balancing apparatus and is configured to carry dialysate away from the balancing apparatus into the second drain, a second discharge line that leads away from the balancing apparatus and is configured to carry dialysate away from the balancing apparatus into the dialysate chamber of the dialyser, a second feed line that leads to the balancing apparatus and is configured to supply dialysate from the dialysate chamber into the balancing apparatus, and an ultrafiltrate line that branches off of the second feed line and leads to the first drain, wherein the ultrafiltration apparatus comprises an ultrafiltrate pump joined to the ultrafiltrate line, the ultrafiltrate pump comprises a pressure source, a flexible membrane, and a pumping chamber, the first obturating member is arranged in a portion of the ultrafiltrate line that leads from the second feed line to the ultrafiltrate pump, and the second obturating member is arranged in a portion of the ultrafiltrate line that leads away from the ultrafiltrate pump and to the first drain, and wherein the ultrafiltrate pump, the first obturating member, the second obturating member, and the ultrafiltrate line are configured to operate in four different operating mode and phase combinations comprising a first operating mode suction phase, a first operating mode pressure phase, a second operating mode suction phase, and a second operating mode pressure phase, during the first operating mode suction phase the first obturating member is open such that the pumping chamber of the ultrafiltrate pump is in fluid communication with the dialysate circuit, the second obturating member is shut such that the fluid communication from the pumping chamber to the first drain is closed, and the pressure on the blood-side of the semipermeable membrane is higher than the pressure on the dialysate-side of the semipermeable membrane of the dialyser such that a predetermined amount of fluid is removed from the extracorporeal blood circuit via the semipermeable membrane of the dialyser, during the first operating mode pressure phase, subsequent to the first operating mode suction phase, the second obturating member is open such that the pumping chamber of the ultrafiltrate pump is in fluid communication with the first drain, and the first obturating member is shut such that the fluid communication between the pumping chamber and the dialysate circuit is closed, during the second operating mode suction phase, the first obturating member is open such that the pumping chamber of the ultrafiltrate pump is in fluid communication with the dialysate circuit and the second obturating member is shut such that the fluid communication from the pumping chamber to the first drain is closed, during the second operating mode suction phase, the first obturating member is open such that the pumping chamber of the ultrafiltrate pump is in fluid communication with the dialysate circuit and the second obturating member is shut such that the fluid communication from the pumping chamber to the first drain is closed, and the second operating mode suction phase and the second operating mode pressure phase are operated such that the pressure on the blood-side of the semipermeable membrane is, at successive intervals, alternately higher and lower than the pressure on the dialysate-side of the semipermeable membrane of the dialyser such that fluid is continuously removed from and, respectively, supplied to the extracorporeal blood circuit via the semipermeable membrane.

2. The extracorporeal blood treatment device according to claim 1, further comprising an input unit for selecting the first operating mode suction phase and the first operating mode pressure phase, or selecting the second operating mode suction phase and the second operating mode pressure phase.

3. The extracorporeal blood treatment device according to claim 1, wherein the dialysate circuit further comprises a bypass line which connects the second discharge line to the second feed line.

4. The extracorporeal blood treatment device according to claim 1, further comprising a control unit configured to control the ultrafiltrate pump, the first obturating member, and the second obturating member, in the first operating mode suction phase, the first operating mode pressure phase, the second operating mode suction phase, and the second operating mode pressure phase.

5. The extracorporeal blood treatment device of claim 1, further comprising a joining line fluidly connecting the pumping chamber to the ultrafiltrate line in between the first obturating member and the second obturating member.

6. The extracorporeal blood treatment device of claim 1, wherein the ultrafiltrate line contains ultrafiltrate resulting from ultrafiltration during a dialysis treatment.

7. The extracorporeal blood treatment device of claim 1, wherein the first obturating member is a first valve and the second obturating member is a second valve.

8. A method for operating an extracorporeal blood treatment device, wherein the extracorporeal blood treatment device comprises a dialyser, comprising a blood chamber, a dialysate chamber, a blood chamber inlet, a blood chamber outlet, a dialysate chamber inlet, a dialysate chamber outlet, and a semipermeable membrane, the blood chamber and the dialysate chamber being divided from one another by the semipermeable membrane, an extracorporeal blood circuit comprising a blood pump and the blood chamber of the dialyser, and a dialysate circuit comprising a dialysate pump, the dialysate chamber of the dialyser, an ultrafiltration apparatus, a first drain, a second drain, a first obturating member, a second obturating member, a balancing apparatus, a first feed line that leads to the balancing apparatus and is configured to supply dialysate from a dialysate source into the balancing apparatus, a first discharge line that leads away from the balancing apparatus and is configured to carry dialysate away from the balancing apparatus into the second drain, a second discharge line that leads away from the balancing apparatus and is configured to carry dialysate away from the balancing apparatus into the dialysate chamber of the dialyser, a second feed line that leads to the balancing apparatus and is configured to supply dialysate from the dialysate chamber into the balancing apparatus, and an ultrafiltrate line that branches off of the second feed line and leads to the first drain, wherein the ultrafiltration apparatus comprises an ultrafiltrate pump joined to the ultrafiltrate line, the ultrafiltrate pump comprises a pressure source, a flexible membrane, and a pumping chamber, the first obturating member is arranged in a portion of the ultrafiltrate line that leads from the second feed line to the ultrafiltrate pump, and the second obturating member is arranged in a portion of the ultrafiltrate line that leads away from the ultrafiltrate pump and to the first drain, and wherein the ultrafiltrate pump, the first obturating member, the second obturating member, and the ultrafiltrate line are configured to operate in four different operating mode and phase combinations comprising a first operating mode suction phase, a first operating mode pressure phase, a second operating mode suction phase, and a second operating mode pressure phase, wherein the method comprises:

passing dialysate through the dialysate chamber via the dialysate pump, the dialysate pump being configured to pump dialysate through the dialysate circuit, passing blood through the blood chamber of the dialyser via the blood pump, the blood pump being configured to pump blood through the extracorporeal blood circuit to thereby treat the blood with dialysate, operating the extracorporeal blood treatment device in the first operating mode suction phase, during which the first obturating member is open such that the pumping chamber of the ultrafiltrate pump is in fluid communication with the dialysate circuit, the second obturating member is shut such that the fluid communication from the pumping chamber to the first drain is closed, and pressure on a blood-side of the semipermeable membrane is higher than the pressure on the dialysate-side of the semipermeable membrane of the dialyser such that a predetermined amount of fluid is removed from the extracorporeal blood circuit via the semipermeable membrane of the dialyser, operating the extracorporeal blood treatment device in the first operating mode pressure phase, subsequent to the first operating mode suction phase, during which the second obturating member is open such that the pumping chamber of the ultrafiltrate pump is in fluid communication with the first drain, and the first obturating member is shut such that the fluid communication between the pumping chamber and the dialysate circuit is closed, operating the extracorporeal blood treatment device in the second operating mode suction phase, during which the first obturating member is open such that the pumping chamber of the ultrafiltrate pump is in fluid communication with the dialysate circuit and the second obturating member is shut such that the fluid communication from the pumping chamber to the first drain is closed, and operating the extracorporeal blood treatment device in the second operating mode pressure phase, during which the first obturating member is open such that the pumping chamber of the ultrafiltrate pump is in fluid communication with the dialysate circuit and the second obturating member is shut such that the fluid communication from the pumping chamber to the first drain is closed, wherein the second operating mode suction phase and the second operating mode pressure phase are operated such that the pressure on the blood-side of the semipermeable membrane is, at successive intervals, alternately higher and lower than the pressure on the dialysate-side of the semipermeable membrane of the dialyser such that fluid is continuously removed from and, respectively, supplied to the extracorporeal blood circuit via the semipermeable membrane.

9. The method according to claim 8, wherein the dialysate is conveyed repeatedly through the dialysate chamber, and the method further comprises:

operating the extracorporeal blood treatment device in the second operating mode suction phase and the second operating mode pressure phase when the dialysate is circulating in the dialysate circuit.

* * * * *